United States Patent [19]

Bucovaz et al.

[11] 4,261,967
[45] Apr. 14, 1981

[54] T-FACTOR, COA-SPC SUBSTANTIALLY FREE OF PROTEOLYTIC ENZYMES AND ITS PREPARATION

[75] Inventors: Edsel T. Bucovaz; John C. Morrison; Walter D. Whybrew; Stanley J. Tarnowski, Jr., all of Memphis, Tenn.

[73] Assignee: Research Corporation, New York, N.Y.

[21] Appl. No.: 900,125

[22] Filed: Apr. 26, 1978

[51] Int. Cl.² .................... A61K 39/00; A61K 43/00; G01N 33/16
[52] U.S. Cl. .................. 424/1; 260/112 R; 424/12; 424/177
[58] Field of Search ............ 424/111.5, 12, 177; 260/112 R

[56] References Cited

U.S. PATENT DOCUMENTS 4,160,817   7/1979   Bucovaz et al. .................. 424/1

OTHER PUBLICATIONS

Bucovaz et al., Proc. Am. Assoc. Cancer Research, 16 (1975), Abstract for Oral Presentation, p. 80.
Tarnowski et al., Abstract from 174th American Chemical Society Meeting, Aug. 28–Sep. 3, 1977.

*Primary Examiner*—Benjamin R. Padgett
*Assistant Examiner*—Christine M. Nucker
*Attorney, Agent, or Firm*—Oblon, Fisher, Spivak, McClelland & Maier

[57] ABSTRACT

CoA-SPC Bakers' yeast extract which is substantially free of proteolytic enzymes.

18 Claims, No Drawings

T-FACTOR, COA-SPC SUBSTANTIALLY FREE OF PROTEOLYTIC ENZYMES AND ITS PREPARATION

BACKGROUND OF THE INVENTION

1. Field of the Invention

This invention relates to improved procedures for preparing CoA-SPC. Moreover, it relates to a low molecular weight substance which solubilizes the CoA-SPC contained in crude Bakers' yeast cell lysate.

2. Description of the Prior Art

Morrison et al in U.S. patent application Ser. No. 727,633, filed Sept. 29, 1976, discloses and claims a method of screening individuals for the presence of cancer. This screening test is reliable and is capable of detecting cancer at early stages of development, before any easily visible observable symptoms have appeared. Morrison et al discovered that the blood serum of individuals having cancer contained the B-protein associated with cancer. Thus, by simply analyzing blood serum for the B-protein it is possible to determine if an individual has cancer or not before any visible symptoms appear.

One detection technique disclosed by Morrison et al relies upon a reagent which comprises CoA-SPC (Coenzyme A-Synthesizing Protein Complex) Bakers' yeast extract and subtracts which interact with this extract to produce a binding protein. This binding protein is capable of binding to protein in the blood serum of humans to form a complex. The properties of this complex depend upon whether or not the B-protein is present. Thus, the use of this reagent provides a simple technique for screening individuals for cancer.

The techniques disclosed by Morrison et al for the preparation of the CoA-SPC Bakers' yeast extract produces a material containing a significant quantity of impurities, in particular, other proteins which are present in the Bakers' yeast. The purification procedures described by Morrison et al are time consuming and expensive.

The storage characteristics of CoA-SPC prepared by the prior art technique is unsatisfactory. When the CoA-SPC is lyophilized and stored, it loses a significant portion of its activity. In addition, the activity of CoA-SPC which is stored frozen at −20 decreases unacceptably with the passage of time.

Tarnowski et al is an abstract distributed at the 174th American Chemical Society Meeting held Aug. 28—Sept. 3, 1977, entitled "Preparation of the Yeast Component of the B-Protein Assay," disclosed that the CoA-SPC and other insoluble protein components of Bakers' yeast cells are solubilized by a component of the supernatant fraction. However, the CoA-SPC Bakers' yeast extract prepared by this technique contains CoA-SPC in a mixture with other proteinaceous materials.

Accordingly, a need exists for a procedure which prepares CoA-SPC Bakers' yeast extract in high purity using comparatively simple procedures.

SUMMARY OF THE INVENTION

Accordingly, an object of this invention is to provide a procedure for preparing CoA-SPC Bakers' yeast extract having a reduced content of other components of the Bakers' yeast, in particular, other proteinaceous materials.

Another object of this invention is to provide a procedure which produces a Bakers' yeast extract having the desired level of CoA-SPC activity in shorter processing times than was possible previously.

Still another object of the present invention is to provide a procedure for isolating from Bakers' yeast the component or components which solubilize the CoA-SPC.

Yet another object of the present invention is the characterization of the component or components which solubilize the CoA-SPC contained in Bakers' yeast cells.

Still another object of the present invention is CoA-SPC Bakers' yeast extract of high purity.

Another object of this invention is CoA-SPC Bakers' yeast extract which is substantially free of proteolytic enzymes.

Yet another object of this invention is to prepare a storage stable CoA-SPC Bakers+ yeast extract.

Another object of this invention is to prepare a CoA-SPC Bakers' yeast extract which can be lyophilized and stored with only a minimal loss of activity.

These and other objects of the present invention have been achieved by the following procedures:

It has been discovered that CoA-SPC having a satisfactory purity can be prepared by freezing and subsequently thawing Bakers' yeast. The resulting liquid and solid phases are separated. The solid phase is then subjected to conditions which preferentially solubilize insoluble proteinaceous materials other than the CoA-SPC which are bound to solid phase yeast material. The resulting solubilized proteinaceous materials are separated from the solid phase containing the insoluble CoA-SPC. The CoA-SPC is solubilized by contacting this solid phase with the liquid phase which was originally formed upon thawing of the yeast. The solubilized CoA-SPC is then removed. The CoA-SPC prepared in this manner contains far less extraneous proteinaceous material than does conventionally prepared CoA-SPC.

In another embodiment of this invention the low molecular weight components of the liquid phase which results from the thawing of the Bakers' yeast are separated from the higher molecular weight components of this phase. These lower molecular weight components are then used to solubilize the CoA-SPC contained in the solid phase after it has been treated to remove other insoluble proteinaceous materials.

Yet another embodiment of this invention is the low molecular weight cellular component of Bakers' yeast which solubilizes CoA-SPC, called the t-factor.

DETAILED DESCRIPTION OF THE PREFERRED EMBODIMENTS

The low molecular weight component of Bakers' yeast which solubilizes the CoA-SPC found in the Bakers' yeast cells, hereafter the "t-factor", may be prepared by any of the conventional procedures designed to lyse Bakers' yeast cells, or the procedures which extract cellular materials from the yeast cell, such as sonication, homogenization, French Press, lytic enzymes followed by osmotic shock, and also boiling the yeast in $H_2O$.

Commercially available Federal Brand, Budweiser, Fleischmann and Kyowa Hakko Kogyo Co., Ltd. Shizucka, Japan yeasts have been successfully used.

Preferably the t-factor is prepared either (1) by freezing the yeast in an ether-$CO_2$ mixture as described by Morrison et al in U.S. application Ser. No. 727,633, for the preparation of CoA-SPC; or (2) freezing Bakers' yeast, preferably crumbled, in liquid N$_2$ to freeze the cells and subsequently thawing.

In either technique (1) or (2) it is necessary to separate the solid and liquid phases if purified CoA-SPC Bakers' yeast extract is desired. If a purified product is not desired, the thawed material from technique (2) can be added directly to the solid portion obtained in technique (1). The thawed mixture of technique (1) can be directly processed to produce impure CoA-SPC Bakers' yeast extract, but is not preferred.

When technique (1) is employed and CoA-SPC Bakers' yeast extract is also to be recovered, the separation technique must be capable of separating the t-factor which is in the liquid phase from the solid phase which contains the insoluble CoA-SPC and other insoluble proteinaceous materials to produce the CoA-SPC-containing phase which is substantially free of the t-factor. Suitable separation techniques include centrifuging, ultrafiltration, column chromatography and the like. If desired, the thawed yeast sample may be subjected to a first separation to remove intact yeast cells by an suitable technique including decantation, low speed centrifugation and the like. The preferred separation technique involves relatively high speed centrifugation, preferably at a minimum of 4,000 to 5,000×g, preferably at least 10,000×g, and most preferably at about 105,000×g or greater. The centrifuging should be conducted for a period sufficient to achieve the necessary separation. At higher centrifuging speeds this time is obviously lower than at the lower centrifuging conditions. The time can range from 10 minutes to as long as 2 hours, obviously longer centrifuging times may be used but offer no advantage. Generally, centrifuging for about one (1) hour is sufficient. If CoA-SPC Bakers' yeast extract is not to be produced or it is not desired to produce the extract in high purity, then it is not necessary to prepare a CoA-SPC containing phase which is essentially free of t-factor. Thus, in this case, less vigorous separation techniques may be used.

The supernatant fraction from the centrifugation may be used as is as the source of the t-factor to solubilize the CoA-SPC. However, it is preferred to further purify the t-factor prior to use. The additional purification may comprise denaturing followed by decanting and additional centrifugation. The denaturing is preferably achieved by heating the supernatant fraction containing the t-factor to a temperature sufficient to denature the heat denaturable components of the fraction. The temperature and time of denaturing is not critical, higher temperatures allow for shorter heating times. Typical denaturing is conducted at from 50° to 100° C. for times ranging from 3 minutes to 24 hours. Temperatures of about 80° C. for periods of about five minutes have satisfactory results. If desired, the denatured supernatant containing the t-factor may be centrifuged and then recovered. The speed of the centrifugation is not critical and may range from 5,000×g to 105,000×g, centrifuging at 105,000×g or greater has proven satisfactory. The centrifuging time is not critical and may range from 10 minutes to 2 hours. Centrifuging periods of about one (1) hour have proven satisfactory. The resulting supernatant contains t-factor which is essentially free of heat denaturable proteins.

If desired, the supernatant fraction may be subjected to further treatments to increase the purity of t-factor. Such treatments can include filtration and ultrafiltration, dialysis, paper or column chromatography, precipitation or any combination thereof to yield a fraction substantially free of material having molecular weight greater than 25,000, preferably substantially free of material having a molecular weight greater than 1,000, most preferably substantially free of material having a molecular weight greater than 1,000 and less than 400. The t-factor itself has a molecular weight of less than 1,000. Based on ultrafiltration, the molecular weight is less than 500. Based on Sephadex Chromatography, the molecular weight is between 400 and 1,000. The discrepancy is probably a result of the ultrafiltration membrane having a higher molecular weight cut off than 500. The membrane has been found to allow CoA which has a molecular weight of about 800 to pass through at the same rate as a compound with a molecular weight of 500 or less. Accordingly, the molecular weight of the t-factor is most probably between 400 and 1,000.

When this technique is used to prepare the t-factor, it is possible to treat the solid material which is recovered from the initial separation of liquid and solid phase from the thawed yeast to recover CoA-SPC therefrom. The recovery will be subsequently described in detail.

The second procedure for preparing t-factor comprises freezing the yeast under cryogenic conditions such as by introducing the Bakers' yeast, preferably in crumbled form, into liquid nitrogen to freeze the cells. The period of immersion in liquid nitrogen is not critical so long as it is for a time sufficient to freeze the cells. It may range from 5 minutes to 1 hour, though longer times may be used, no advantage is gained therefrom. Shorter times can be used if the cells are frozen.

The frozen cells are subsequently thawed. The thawed mixture contains lysed cells, intact cells and soluble cellular components from both. The solid and liquid fractions are separated since the t-factor is principally in the liquid phase, using conventional techniques such as centrifuging, filtering, dialyzing and the like. Preferably, the separation is achieved by centrifuging at a speed and time sufficient to achieve the separation. The speed of centrifuging is preferably at least 4,000×g, more preferably, at least 10,000×g, and most preferably at about 105,000×g. The period of centrifuging is dependent upon the force. Generally, the centrifuging is performed for at least 10 minutes, preferably for at least 30 minutes. Centrifuging for one hour at 105,000×g, has proven satisfactory, although longer or shorter periods may be used.

The liquid fraction thus recovered may be used directly as the source of t-factor to solubilize the CoA-SPC in the yeast cells. Preferably, however, the supernatant fraction containing the t-factor is subjected to further purifications such as denaturing, dialysis, filtration, ultrafiltration, precipitation and chromatography. Combinations of these purification procedures may also be used. The purification procedure must be performed such that the fraction containing the low molecular weight constituents is retained since the t-factor appears to have a comparatively low molecular weight, probably 1000 or less.

The preferred purification procedure comprises first denaturing the denaturable proteins in t-factor-containing supernatant. The denaturing is most preferably accomplished by heating at temperature and time sufficient to denature the heat denaturable proteins. Generally, temperatures of from 50° to 100° C. may be used, preferably from 75° to 85° C. The period for which the mixture is heated is dependent upon the temperature, but generally ranges from 3 minutes to 24 hours. The period of heating is chosen such that the desired denaturing is obtained. At temperatures of about 80° C., heat treatment times of 5 to 10 minutes have proven satisfactory. The resulting mixture may be used as the source of t-factor to solubilize the CoA-SPC. Preferably, however, the mixture is treated to remove the denatured proteins.

The denatured proteins may be removed using conventional techniques such as centrifuging, filtering, dialysis and the like. Centrifuging is preferred because of its simplicity. The centrifuging which may be used are those employed previously to separate the liquid and solid phases. Centrifuging at about 105,000×g for about 30 minutes has proven satisfactory.

The resulting supernatant may be used directly as the source of t-factor for the CoA-SPC solubilization. However, it is preferable to remove any high molecular components before using the supernatant as the t-factor source. Preferably, those components having a molecular weight greater than 25,000 are removed, more preferably those with a molecular weight above about 1,000 are removed. Thus, the fractions containing components with molecular weights equal to or less than 25,000 preferably of about 1,000 or less and most preferably of molecular weight of 400 to 1,000 are used as the source of t-factor. Such can be prepared using conventional techniques such as filtering, dialysis, ultrafiltration, chromatography, precipitate and combinations thereof. The exact procedure is not critical.

A typical procedure could involve dialysis against reduced pressure utilizing a membrane which retains most components having a molecular weight greater than 15,000 to 20,000. The reduced pressure is not critical and may range from 12 to 700 mm Hg. The t-factor activity is possessed by the dialysate. Alternatively, the supernatant may be filtered utilizing a medium which retains materials having a molecular weight of 25,000 or greater. The t-factor is in the filtrate. Either of the dialysate or the filtrate may be used directly as the source of t-factor for the solubilization of CoA-SPC.

Preferably, the dialysate or filtrate is subjected to ultrafiltration and chromatography to remove materials having a molecular weight of greater than 1000 or less than 400. The filtrate is then utilized as the source of t-factor to solubilize the CoA-SPC. Using the techniques described it is possible to obtain t-factor of the desired purity. After simply denaturing by heating the t-factor containing supernatant as described previously, a purification of 1.5 fold is obtained. Filtering to remove from the denatured material the fraction having a molecular weight greater than 25,000 results in t-factor having a purity of about 3 fold. Unpurified t-factor may be used to solubilize the CoA-SPC from the yeast cells, however, t-factor of at least 1.5 fold purity is preferred, more preferably t-factor with a purity of at least 3 fold is used. It is possible to prepare t-factor having a purity of up to 900 fold if desired and this may be used to solubilize CoA-SPC. T-factor having a purity of from 540 to 625 fold can be readily obtained. However, such high purity t-factor is not necessary to prepare the CoA-SPC of high purity of this invention.

The t-factor purity is calculated as follows:

$$\frac{\text{Weight of total solids in crude supernatant sufficient to yield 1 ml of purified } t\text{-factor}}{\text{Total solid weight in 1 ml of recovered, purified } t\text{-factor}} = \text{fold of purity}$$

The CoA-SPC Bakers' yeast extract is prepared by freezing the Bakers' yeast in a $CO_2$-ether mixture as described in Morrison et al or in a liquid nitrogen-ether mixture. In these procedures, other organic solvents which do not inactivate CoA-SPC may be used. Preferably these solvents are easily removable from the lysed cells after thawing. Suitable solvents include acetone, toluene, chloroform, butanol and the like may be used in place of ether. The temperatures to which the yeast is exposed are those at which the yeast freezes, preferably the temperature of the mixture is from $-70°$ to $-195°$ C., preferably from $-72°$ to $-77°$ C. The period for which the yeast is subjected to these temperatures is dependent upon the temperature and the quantity of the yeast. The period need be only for a time sufficient to freeze the yeast cells, extended periods may be used if desired. The frozen yeast is then thawed. If an ether mixture was used to freeze the yeast, the residual ether is removed. The insoluble CoA-SPC is contained in the solid phase while the t-factor is contained in the liquid phase. The two phases are separated under conditions such that the solid phase is essentially free of t-factor. Suitable separation techniques are those described previously for the preparation of t-factor by technique (1).

The cellular material recovered contains only insoluble CoA-SPC but also other insoluble proteinaceous materials as well as other impurities. Since the presence of t-factor is necessary to solubilize the CoA-SPC, but not the other insoluble proteinaceous materials, it is possible to selectively solubilize these other insoluble proteinaceous components of the yeast. This insolubilization can be accomplished by simply agitation, agitation in an aqueous medium and the like. The rate and degree of solubilization can be increased by the addition of salts such as chlorides, nitrate, acetate and the like. Preferably, an aqueous medium containing chloride ions is utilized. The cation moiety of the salt may be any cation which does inhibit CoA-SPC activity. Thus, the salts of mercury, lead, zinc, iron and lithium should be avoided. However, other salts may be used. Potassium, sodium, magnesium, calcium and manganese salts have all been used successfully. In particular, KCl, NaAc, tris buffer and the like may be used. Appropriate selection of the agitation time and anion concentration allows one to remove as much or as little of these other proteinaceous materials as may be desired. Generally, anion, preferably chloride ion, concentrations of from 0.01 to 2.0 N have proven satisfactory, preferably from 0.026 to 1.0 N, and most preferably from 0.47 to 0.73 N. Higher concentrations of anion may be used but offer no particular advantage. Regardless of ion concentration, active CoA-SPC is not solubilized in the absence of t-factor.

The pH of the medium during the solubilization of these other insoluble proteinaceous materials is not critical and may be acid, basic or neutral pH. Preferably the pH ranges from 5.0 to 8, most preferably from 5.6 to 5.9

The pH may be maintained by addition of essentially any buffer, acid or base, such as tris acetate and NaAc.

The thus solubilized proteinaceous material is separated from the cellular material containing the insoluble CoA-SPC by conventional techniques such as centrifugation at 10,000 to 105,000×g for 30 minutes, and decantation of the supernatant liquid containing the extraneous protein, filtration and and the like.

The recovered cellular material may, if desired, be washed with water to remove any residual impurities or soluble proteinaceous materials not removed by the separation procedure. The washed cellular material is then introduced into an aqueous medium containing chloride or nitrate ions. The source of chloride or nitrate ions is not critical and includes those mentioned previously. The concentration of chloride or nitrate ions influences the rate at which the t-factor solubilizes the CoA-SPC. Accordingly, it is desirable to have a minimum chloride or nitrate ion concentration of 0.02 N. Lower concentrations will work but the rate of solubilization will be low. The maximum chloride or nitrate ion concentration is approximately 2 N (75 mg/ml.). Since the CoA-SPC or t-factor source or both will probably contain some endogenous chloride ions, it is not essential to add chloride or nitrate ions to the aqueous medium. It is preferred, however, to adjust the chloride ion concentration to at least 0.40 N or add sufficient nitrate ions to achieve this concentration and to achive a satisfactory solubilization rate. Most preferably the chloride or nitrate ion concentration will range from 0.47 to 0.73 N.

The pH of the aqueous medium during the solubilization of the CoA-SPC is not critical. Preferably the pH ranges from 5 to 8, more preferably from 5 to 6, and most preferably it is from 5.6 to 5.9. The pH can be adjusted by addition of suitable acids, bases or buffers, such as NaAc and tris acetate. However, the pH need not be adjusted and water alone can be utilized in the solubilization.

The quantity of the t-factor or t-factor-containing extract which is added is not critical. However, the rate at which the CoA-SPC is solubilized is a function of the quantity of t-factor present. The amount of t-factor utilized to solubilize the CoA-SPC may be that which was recovered during the initial processing steps of the Bakers' yeast. The t-factor may be added in the form of the supernatant which was originally separated from the thawed cellular material. The total quantity of this supernatant may be added or a fraction thereof, such as ½, ¼, ⅛, ⅜, etc. In order to recover CoA-SPC having a high purity it is preferable to utilize a t-factor-containing mixture which has been purified by any of the previously described procedures.

It is possible to recover the t-factor from the solubilized CoA-SPC by dialysis or filtration through a membrane which retains components having a molecular weight greater than 100,000 MW. The filtrate or dialysate can then be treated to obtain purified t-factor using the procedures described previously. If desired, purified t-factor may be obtained directly by dialysis or filtration through a membrane which retains those components having a molecular weight greater than 1,000. By recovering and re-using the t-factor it is possible to use greater quantities of t-factor to solubilize CoA-SPC than are found in the original sample from which the CoA-SPC is being recovered. Thus, t-factor from as many yeast samples as one desires can be retained and used to solubilize CoA-SPC from any quantity of yeast. This procedure provides an economical technique for increasing the solubilization rate. The t-factor used to solubilize the CoA-SPC can be that obtained by procedure (2) described previously.

The CoA-SPC Bakers' yeast extract which is produced by this preferred procedure is essentially free of proteolytic enzymes. The presence of proteolytic enzymes in CoA-SPC Bakers' yeast extracts produced by the prior art procedure resulted in an extract having unsatisfactory storage characteristics. The CoA-SPC Bakers' yeast extract of this invention loses substantially less of its activity upon lypholizing and storage than the prior art extract because its reduced proteolytic enzyme content. The extract of this invention also processes superior storage characteristics when stored frozen at $-20°$ C.

Additionally, the CoA-SPC Bakers' yeast extract of this invention requires less ATP substrate to produce the binding protein utilized in the cancer detection procedure of U.S. application Ser. No. 727,633, filed Sept. 29, 1976. Also, the CoA-SPC Bakers' yeast extract of this invention has improved CoA-SPC activity per mg/protein when compared with that previously available. CoA-SPC Bakers' yeast extract has a molecular weight of about 200,000 and is characterized by its interaction with the substrates L-cysteine, D-pantothenic acid and ATP. It is also characterized by its interaction with L-cysteine, D-pantothenic acid and ATP to produce the binding protein which is capable of complexing with blood serum protein as described in U.S. application Ser. No. 727,633, filed Sept. 29, 1976.

Having generally described this invention, a further understanding can be obtained by reference to certain specific examples which are provided herein for purposes of illustration only and are not intended to be limiting unless otherwise specified.

EXAMPLE 1

Assay for CoA-SPC Activity

CoA-SPC activity was determined using either L-cysteine, D-pantothenic acid or ATP as the radioactive tracer. A typical reaction mixture contained: 4.70 mM disodium ATP, 0.5 ml buffer A (containing 0.10 M trisacetate, pH 7.2, 0.02 M magnesium acetate 0.05 M KCl), 0.50 mM calcium salt of D-pantothenic acid, 0.50 mM of [$^{35}$S]-L-cysteine (18,000 cpm), 0.05 ml of the supernatant fraction to be assayed and water to a total volume of 1 ml. Reaction mixtures without ATP served for background activity.

Tubes containing the reaction mixture were incubated at 36° C. for one hour. The reaction was terminated by adding 2 ml of 10% TCA and heating the tubes in a boiling water bath for five minutes. The tubes were cooled and the denatured protein precipitates containing the CoA-SPC were recovered by filtration using a Millipore filtering apparatus and Whatman No. 3 MM paper discs. The precipitates collected on the discs were washed four times with approximately 2 ml of water per wash. The discs were dried and then transferred to scintillation vials, and the radioactivity present measured in a Nuclear Chicago Liquid scintillation counter using the scintillation liquid described by Hoskinson and Khorana in J. Biol. Chem, 240 pages 2129–2135 (1965).

Assay for t-Factor Activity

The assay procedure used to detect the presence of t-factor is as follows:

The fraction to be tested for t-factor activity was stirred for 17 hours at 4° C. with washed pellet material recovered from the crude yeast cell lystate by centrifugation at 105,000×g for 1 hour, and KCl was added to a final concentration of 5 mg/ml. Following the stirring step, the mixture was centrifuged at 105,000×g for one hour, and the supernatant liquid was assayed for CoA-SPC activity as previously described. For control samples pellet material were stirred for 17 hours with 0.05 M Tris-acetate, Ph 7.2 containing 5 mg/ml KCl, and with the 105,000×g supernatant fraction in the absence of exogenous KCl.

Preparation of t-Factor

Approximately 454 g of fresh Bakers' yeast were crumbled into a suitable container containing 0.7 kg of anhydrous ethyl ether. Compressed $CO_2$ (3 kg) was added to freeze the yeast. The frozen yeast was thawed at 23°–24° C. for 7 hours. Residual ether and $CO_2$ were removed from the thawed yeast cell lysate by vacuum as previously described in *Morrison et al.*

The yeast cell lysate was divided into three equal parts and treated according to the following procedures. One-third of the lysate, Procedure I, remained as a crude lysate. The second one-third of the lysate, Procedure II, was centrifuged at 105,000×g for 1 hour and the supernatant saved. The final portion of the yeast cell lysate, Procedure III, was centrifuged at 1,000 ×g for 10 minutes at 4° C. to remove intact yeast cells. The cells were discarded, and the remaining suspension was centrifuged at 105,000×g for 20 minutes at 4° C. Both pellet and supernatant fraction were saved. The supernatant fraction was heated at 80° C. for five minutes centrifuged at 105,000×g for one hour and decanted through cheesecloth and saved. The pellet material was resuspended two times in 0.05 M Tris-acetate, pH 7.2, and centrifuged successively at 105,000×g for one hour to wash the pellet material. A portion of the washed pellet material, Procedure IIIa, was resuspended in the 105,000×g heated supernatant fraction as in Procedure III. Another portion of the washed pellet material, Procedure IIIb, was suspended in 0.05 M Tris-acetate, pH 7.2. A final concentration of approximately 5 mg/ml of exogenous KCl was added to Procedures I, II, IIIa and IIIb, and mechanical stirring was then initiated and continued at 4° C. for 17 hours.

Following the 17 hour stirring step, which gradually solubilized CoA-SPC, the mixtures form Procedure I, II, IIIa, and IIIb were centrifuged at 105,000×g for one hour separating pellet and supernatant fraction. Each supernatant fraction was assayed for CoA-SPC activity using either L-cysteine, D-pantothenic acid or ATP as the radioactive tracer.

Procedure I and Procedure IIIa contained CoA-SPC activity as determined by the amount of measurable radioactivity incorporated into the TCA precipitates. Procedure IIIb, which contained washed pellets mixed with 0.05 M Tris-acetate, pH 7.2 and Procedure II, were void of CoA-SPC activity. Consequently, it would appear that a component (s) present in the supernatant fraction is required to solubilize CoA-SPC.

The evidence presented contains two vitally important characteristics of CoA-SPC. (1) CoA-SPC appears to be bound to extremely heavy, insoluble yeast cell component (s), and will remain in that state unless conditions described under Procedure I and Procedure IIIa above are followed; (2) a soluble component of the yeast cell is essential for the release or solubilization of CoA-SPC. Because this soluble cellular component had not been identified, it has tentatively been named t-factor.

EXAMPLE 2

Bakers' yeast (454 g.) is crumbled into liquid $N_2$ to freeze the cells. The frozen cells are then thawed and the thawed mixture contains lysed cells, intact cells and soluble cellular components from both. This mixture is centrifuged at 105,000×g at 4° C. for one hour. The liquid fraction is decanted into another vessel and heated at 80° C. for 10 minutes to remove heat denaturable proteins from the mixture. Following the heating procedure, the mixture is centrifuged again at 105,000×g for 30 minutes. The supernatant liquid obtained is dialysed using No. 8 tubing against reduced pressure, from 700 to 12 mm Hg. All detectable t-factor activity is present in the dialysate. For some preparations an alternate step to dialysis is used. The heated supernatant fraction is filtered, rather than dialyzed, through Amicon Centriflo filter cones (CF25) that retain materials of 25,000 mw or greater. In this case, t-factor appears in the filtrate. Either the dialysate or the filtrate containing t-factor is subjected to two successive ultrafiltration steps. The first ultrafiltration step utilizes an Amicon UM-2 filter (1,000 mw retention). The second ultrafiltration step involves passing the UM-2 filtrate, which contains t-factor, through an Amicon UM-05 membrane (500 mw retention). The t-factor was present in the UM-05 filtrate. On the basis of the ultrafiltration steps, it would appear that t-factor has a molecular weight of 500 or less, however, it is known that certain compounds such as CoA, with a molecular weight of 800 pass through this filter. Column chromatography indicates that the t-factor has a molecular weight of between 400 to 1,000.

CoA-SPC activity has not been demonstrated prior to its solubilization; therefore, testing for t-factor activity is by indirect assay based on the presence of CoA-SPC activity after solubilization. The amount of CoA-SPC activity present after 17 hour stirring appears to be directly related to the concentration of t-factor present in the fraction tested.

EXAMPLE 2

Trypsin and Protease Treatment of t-Factor

The apparent CoA-SPC solubilizing ability of t-factor may suggest t-factor functions as a proteolytic enzyme. A portion of the Amicon UM-05 filtrate was lyophilized in 4 ml aliquots. One aliquot of the filtrate was dissolved in 10 ml of 0.13 M ammonium bicarbonate, and to this 100 µg of trypsin (Worthington, 2×crystallized) was added. The pH of the solution was adjusted to 8.0 with 1 N $NH_4OH$. A control sample was prepared in a similar manner, except the trypsin was inactivated by boiling for 2 minutes prior to its addition to the lyophilized UM-05 filtrate. Two additional aliquots were subjected to protease (Sigma, *Strep. griscus*, repurified Type VI) digestion. To one aliquot of the lyophilized filtrate, dissolved in 10 ml of 0.13 M ammonium bicarbonate, 100 µg of protease was added and the pH adjusted to 7.2 with 1 N HCl. A control for protease was prepared identically, except the enzyme was boiled for 2 minutes prior to its addition to the lyophilized UM-05 filtrate. All four samples were incubated 6 hours at 36° C. and the pH monitored. Following the incubation period, the enzymatic reactions were terminated by boiling for 3 minutes. Denatured proteolytic enzymes were removed by centrifugation, and the supernatant liquids were dialyzed at 4° C. against reduced pressure through No. 8 tubing. The dialysates were lyophilized to dryness and dissolved in 4 ml $H_2O$. The pH was adjusted to 5.8, if necessary, with 1N HCl. Potassium chloride was added to a final concentration of 5 mg/ml, and the dialysates were mixed with washed pellet material obtained from the $CO_2$-ether preparation method. Assaying for CoA-SPC activity revealed that trypsin and protease controls had activity. In addition, the reaction mixtures in which trypsin and protease had not been inactivated had the same level of CoA-SPC activity. The evidence presented is highly suggestive that t-factor does not contain peptide bonds.

Heat Treatment of t-Factor

The UM-05 filtrate was also tested for stability to heat. Table I shows that less than a 10% decrease in t-factor activity was observed after heating at 80° C. for 24 hours. Consequently, it would appear, particularly since the detectable loss in t-factor activity took place during the first 10 minute heating, that t-factor is stable under these conditions. Any observed losses in t-factor activity appears to be due to inherent characteristics of the procedure.

Requirement for KCl or Chloride Ion

Exogenous cloride or nitrate ions and t-factor appear to be essential for maximum solubilization of CoA-SPC (Table I). Because of the presence of endogenous chloride ions in the fractions containing t-factor, some CoA-SPC activity was detected without the addition of chloride to the stirring flask. However, KCl in H₂O or in 0.05 M tris acetate, pH 7.2 in the absence of t-factor did not release CoA-SPC. It is believed that t-factor is specific for the release of CoA-SPC, however, the amount of protein present in the supernatant fraction following stirring pellet material with t-factor and KCl is greater than the amount of protein which could be accounted for by CoA-SPC alone. Therefore, extraneous protein is also solubilized. It is known that much of the extraneous protein solubilized is due to mechanical stirring and salt concentration.

As demonstrated in Table I, it is the chloride or nitrate ion which appears to be essential for the solubilization of CoA-SPC and not the cation. Mono and dichloride salts at equivalent chloride ion concentrations were shown to function equally as well in the solubilization of CoA-SPC. The addition of salts not containing chloride or nitrate (e.g., KAc, NaAc, Na₂SO₄) did not elevate the level of CoA-SPC activity above that indicated for endogenous chloride. Consequently, it would appear that the salts tested not containing chloride or nitrate ions were not functional in the solubilization of CoA-SPC. The chloride or nitrate ions may be added in any conventional form, such as the form of a salt. However, cations such as Li, Hg, Pb, Zn and Fe, appear to inhibit the catalytic activity of CoA-SPC. Cations such as K, Na, Mn, Mg, and Ca have all proven suitable.

In other studies, experiments were conducted using [$^{36}$Cl]-NaCl to determine if the chloride ion exerts its action by binding to CoA-SPC, heavy components of the yeast cell lysate or t-factor. Results of these experiments did not indicate that $^{36}$Cl$^-$ was binding to any of these fractions.

TABLE I

Effect of Various Salts on the Solubilization of CoA—SPC

| Components Added[1] | | CoA—SPC Activity |
|---|---|---|
| t-Factor | Salt | mμ moles |
| + | — | 5.2 |
| + | KCl | 19.8 |
| — | KCl[2] | 0.5 |
| + | NaCl | 18.2 |
| + | MgCl₂ | 19.3 |
| + | CaCl₂ | 25.0 |
| + | MnCl₂ | 29.3 |
| + | LiCl[3] | 0.3 |
| + | KC₂H₃O₂ | 7.6 |
| + | NaC₂H₃O₂ | 4.9 |
| + | KI | 3.1 |
| + | Na₂SO₄ | 5.2 |
| + | KNO₃ | 18.9 |
| + | Ca₃(PO₄)₂ | 0.1 |
| — | CaCl₂ | 0.2 |

[1] (+) indicate t-factor added, (−) indicate either t-factor or salt is omitted from the mixture. The average endogenous Cl concentration based on several batches of yeast was 0.92 mg/ml of the 105,000 xg supernatant fraction of the cell lysate. The 5 mg/ml of exogenous KCl added is based on the total yeast cell volume. This is equivalent to 25 mg/ml exogenous KCl for the 105,000 xg supernatant fraction. Other salt tested were adjusted to approximately the KCl concentration.
[2] KCl in the absence of t-factor was dissolved in 4 ml of H₂O and then mixed with pellet material as described under "Assay for t-Factor Activity".
[3] Anions associated with cations such as Li, Hg, Pb, Zn, Fe appear to inhibit the catalytic activity of CoA—SPC.

Therefore if $^{36}$Cl$^-$ binding does take place, the bond between $^{36}$Cl$^-$ and its site of binding is broken during the recovery of CoA-SPC, other cell components or t-factor for assay.

Moreover, t-factor does not appear to exert its action by forming a stable bond with CoA-SPC or other cellular components, because following solubilization of CoA-SPC, t-factor can be recovered several times by dialysis and reused without an apparent loss of activity.

Bakers' yeast cells contain proteolytic enzymes and other enzymes which may be detrimental to CoA-SPC, its substrate or its product—the binding protein. CoA-SPC as prepared in U.S. application Ser. No. 727,633, filed Sept. 29, 1976, contains substantial quantities of these enzymes and contains detectable levels of Protease A, B and C. The maximum purity which can be obtained with the procedure disclosed in application Ser. No. 727,633, is about 36 fold. The CoA-SPC of the present invention is purified at least 45 fold, and generally at least 50 fold. Purities of 50 fold are readily obtainable and provide a CoA-SPC which is free of detectable levels of Protease A, B and C. Further, most of the other proteolytic and hydrolytic enzymes whether soluble in vacuoles or in periplasmic spaces are removed by the procedure of this invention to prepare CoA-SPC. Thus, the CoA-SPC Bakers' yeast extract of this invention may be characterized as free of detectable levels of Proteases A, B and C.

The purity of the CoA-SPC is calculated as follows:

$$\frac{\text{counts per minute/mg of purified solution protein}}{\text{counts per minute/mg of crude solution protein}} = \frac{\text{fold}}{\text{of purity}}$$

wherein the counts per minute/mg of solution protein are determined as described in Example 1; wherein, $$\frac{\text{counts/min/ml of solution}}{\text{mg of protein/ml of solution}} = \text{counts/min/mg of solution protein}$$

If desired, the t-factor may be prepared in a very purified form such that it is essentially free of all proteinaceous materials. Consequently, all detectable proteolytic and other enzymes in the soluble portion of the cell lysate, from which the t-factor has been purified, have been removed. In addition, the procedures of this invention removes from the t-factor the endogneous substrate D-pantothenic acid and L-cysteine as well as all other soluble components with a molecular weight of more than 1,000 and less than 400.

The washing of the solid which results from lysing of the yeast cells followed by salt extraction, as described previously, removes the unwanted and undesirable proteinaceous materials such that CoA-SPC of high purity as discussed previously is obtained. This high purity CoA-SPC has been shown to be stable to lypholization and storage and storage at in solutions at −20° C. After storage for four (4) months, the activity of the CoA-SPC had not decreased from its original level. This represents a significant improvement over the CoA-SPC described in U.S. application Ser. No. 727,633. The CoA-SPC prepared in accordance with the procedure described in that application loses from 25 to 100% of activity after storage for similar time periods of about four (4) months.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. Coenzyme A-Synthesizing Protein Complex (CoA-SPC) Bakers' yeast extract which is substantially free of proteolytic enzymes and having a purity of at least 45 fold.

2. The CoA-SPC of claim 1, having a purity of at least 50 fold.

3. t-Factor which is characterized by that fraction of Bakers' yeast having a molecular weight of 400 to 1,000 and which solubilizes insoluble CoA-SPC in the presence of chloride ions and which is essentially free of Bakers' yeast components which are heat denaturable.

4. The t-factor of claim 3, which is substantially free of Bakers' yeast components having a molecular weight of greater than 100,000.

5. The t-factor of claim 3, which is substantially free of Bakers' yeast components having a molecular weight of greater than 1,000.

6. The t-factor of claim 5, which is substantially free of Bakers' yeast components having a molecular weight of less than 400.

7. The t-factor of claim 3, having a purity of at least 1.5 fold.

8. CoA-SPC Bakers' yeast extract free of detectable levels of proteases A, B and C.

9. A reagent for use in detecting the presence of cancer in humans which comprises CoA-SPC Bakers' yeast extract which is substantially free of proteolytic enzymes and amounts of substrates for said extract effective to interact with said extract to produce a binding protein which binds to protein in the blood serum of said human to form a serum-protein/binding protein complex.

10. The reagent of claim 9, wherein said substrates are ATP or a salt thereof, D-pantothenic acid or a salt thereof, and L-cysteine or a salt thereof.

11. The reagent of claim 10, wherein the pH is from 6.2 to 7.6.

12. The reagent of claim 11, wherein at least one of said substrates is radioactively tagged.

13. The reagent of claim 12, which further comprises an amount of a buffer effective to maintain said pH value.

14. The reagent of claim 13, which comprises 0.01 to 10 mM of said ATP or salt thereof; from 0.01 to 1.0 mM of said D-pantothenic acid or salt thereof; and from 0.01 to 0.6 mM of said L-cysteine or salt thereof.

15. The reagent of claim 14, which comprises from 0.01 to 0.1 ml of said extract and up to 0.8 ml of said buffer per ml of reagent.

16. The reagent of claim 12, wherein said radioactive substrate is [$^{35}$S]- or [$^{14}$C-U]-L-cysteine or [$^{14}$C]-D-pantothenic acid.

17. A reagent for use in detecting the presence of cancer in humans which comprises from 0.04 to 0.06 ml of CoA-SPC Bakers' yeast extract substantially free of proteolytic enzymes; from 1.5 to 5 mM ATP or a salt thereof; from 0.5 to 0.6 mM D-pantothenic acid or a salt thereof; from 0.05 to 0.15 mM L-cysteine or a salt thereof; and up to 0.8 ml of a buffer which maintains the pH of the reagent in the range of from 6.5 to 7.2, per 1 ml of solution, the remainder being distilled water; wherein said L-cysteine is in the [$^{35}$S], or [$^{14}$C-U]-radioactive form or said D-pantothenic acid is in the [$^{14}$C]-radioactive form.

18. The reagent of claim 17, wherein ATP is present as the disodium salt, D-pantothenic acid is present as the hemi-calcium salt and the buffer comprises from 0.001 to 250 mM Tris-acetate; from 0.01 to 50 mM magnesium acetate and from 0.001 to 250 mM KCl.

* * * * *